United States Patent [19]

Koyama et al.

[11] Patent Number: 4,517,365
[45] Date of Patent: May 14, 1985

[54] ISOCARBOSTYRIL DERIVATIVE

[75] Inventors: Hiroyasu Koyama, Ageo; Masahiro Tsuji, Ohi; Yoshikuni Suzuki, Ohmiya, all of Japan

[73] Assignee: Nisshin Flour Milling Co., Ltd., Tokyo, Japan

[21] Appl. No.: 390,977

[22] Filed: Jun. 22, 1982

[30] Foreign Application Priority Data

Jun. 25, 1981 [JP] Japan .................... 56-97430

[51] Int. Cl.³ .................. C07D 217/28; A61K 31/47
[52] U.S. Cl. ...................... 546/142; 514/821
[58] Field of Search ......................... 546/142

[56] References Cited

U.S. PATENT DOCUMENTS 4,129,565 12/1978 Fukushima et al. .............. 546/142

FOREIGN PATENT DOCUMENTS 2631080 1/1977 Fed. Rep. of Germany ...... 546/142
57-163367 10/1982 Japan ........................ 546/142
1039874 8/1966 United Kingdom ............. 546/142

*Primary Examiner*—Glennon H. Hollrah
*Assistant Examiner*—James H. Turnipseed
*Attorney, Agent, or Firm*—Abelman, Frayne, Rezac & Schwab

[57] ABSTRACT

Isocarbostyrils of the formula

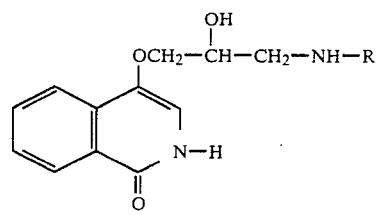

wherein R is a branched alkyl of 3 to 4 carbon atoms, and the acid addition salts thereof, having β-adrenergic blocking activity, are described.

1 Claim, No Drawings

ISOCARBOSTYRIL DERIVATIVE

This invention relates to isocarbostyril derivatives and acid addition salts thereof and to a process for preparing the same. More particularly, the invention pertains to novel isocarbostyril derivatives of the general formula

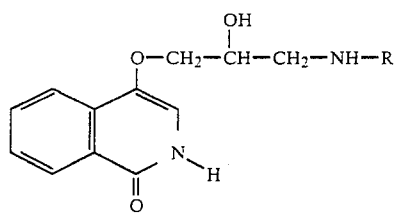

wherein R represents a branched alkyl group having 3 to 4 carbon atoms.

The isocarbostyril derivatives of the general formula (I) and acid addition salts thereof according to this invention have strong β-adrenergic blocking activity and are novel compounds useful for treating heart diseases, e.g. hypertension, stenocardia and arhythmia.

As a compound having β-adrenergic blocking activity and usable for medical treatment of a disease such as hypertension, for example, 4-(3-tertiary-butylamino-2-hydroxy)propoxy-2-methylisocarbostyril hydrochloride of the formula

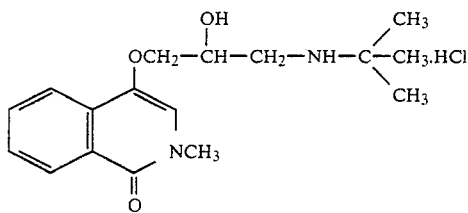

has hitherto been known (cf. British Pat. No. 1,501,149).

It is an object of this invention to provide a compound which is more potent in pharmacological activity than aforeseen known compound, and as a result of extensive investigation to find out such compound we have succeeded in obtaining the compounds of the general formula (I) which are stronger in β-adrenergic blocking activity and longer in duration of action with low toxicity thereby to accomplish the present invention.

In another aspect of the invention, there is provided a process for the preparation of isocarbostyril derivatives, which process comprises reacting 4-hydroxyisocarbostyril of the formula

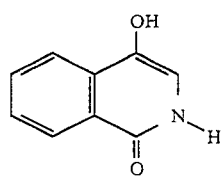

with an epihalogenohydrin of the general formula

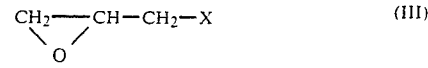

wherein X represents a halogen atom, to obtain a 4-substituted isocarbostyril derivative of the general formula

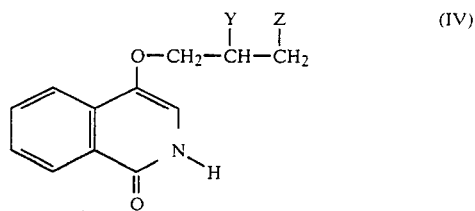

wherein Y represents a hydroxy group, Z represents a halogen atom, or Y may be joined to Z to to form an epoxy ring, and further reacting the 4-substituted isocarbostyril derivative of the formula (IV) thus obtained with an amine of the general formula $$RNH_2 \qquad (V)$$

wherein R is the same as defined above, thereby obtaining an isocarbostyril derivative of the general formula (I). Acid addition salts thereof can be prepared in case of need by reacting said derivative with an acid.

For better understanding, the process of the preparation of isocarbostyril derivatives of the general formula (I) and acid addition salts thereof is described hereinbelow in more details.

The reaction of 4-hydroxycarbostyril of the formula (II) with an epihalogenohydrin of the formula (III) is effected in the presence of an inorganic base such as sodium hydroxide, potassium hydroxide, sodium carbonate, potassium carbonate, metallic sodium or its alcoholate, or an organic base such as piperidine and triethylamine, without using a solvent or with using an organic solvent, e.g. a lower alcohol such as methanol and ethanol, an ether such as tetrahydrofuran and dioxane, an amide such as N-N-dimethylformamide, a ketone such as acetone, or an aromatic hydrocarbon such as benzene and toluene. A lower alcohol is particularly preferable as an organic solvent. The reaction can be carried out at any temperature from room temperature to elevated temperature, and it is usually carried out at a temperature of 35° to 70° C. The reaction time of about 1 to 7 hours is sufficient for the above-specified temperature range.

The amount of epihalogenohydrin used in this reaction is at least in 1-fold mole, preferably 2 to 10 fold moles per 1 mole of 4-hydroxyisocarbostyril of the formula (II). The preferred epihalogenohydrin is epichlorohydrin or epibromohydrin.

Isolation of the product of the general formula (IV) resulted from said reaction can be carried out by silica gel or alumina column chromatography and crystallization. The reaction between 4-substituted isocarbostyril derivative of the formula (IV) with amine of the formula (V) is carried out in the absence of solvent or in the presence of organic solvent, for example, a lower alcohol such as methanol and ethanol, an ether such as tetrahydrofuran and dioxane, an amide such as N,N-dimethyl formamide, and an aromatic hydrocarbon such as benzene and toluene. In this reaction amine of the formula (V) is used at an amount of at least 1-fold mole, preferably 3 to 5-fold moles per 1 mole of 4-substituted isocarbostyril derivative of the formula (IV). And the reaction can be carried out optionally at a temperature of from room temperature to elevated temperature and usually at a temperature within the range of 50° to 100° C. The time of from about 1 to 5 hours or so is sufficient for the reaction. It is possible to concentrate the reaction mass obtained by such process under reduced pressure to obtain the objective product as a crystal of a salt with proper acid and to purify the crystal easily by recrystallization. Hydrochloride, sulfate, phosphate, oxalate, citrate and tartarate can be named as the examples of the aforementioned salts with proper acid.

Isocarbostyril derivatives of the aforementioned general formula (I) include, as typical compounds, 4-(3-tertiary-butylamino-2-hydroxy)propoxyisocarbostyril hydrochloride, 4-(3-secondary-butylamino-2-hydroxy)-propoxyisocarbostyril hydrochloride and 4-(2-hydroxy-3-isopropylamino)propoxyisocarbostyril hydrochloride.

The following experimental tests were conducted to evaluate utility of the compounds of the present invention in comparison with the known compounds. The compounds tested are as follows:

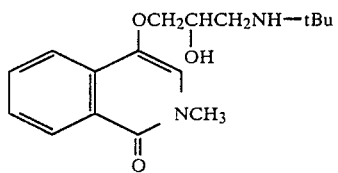

I (Known compound)

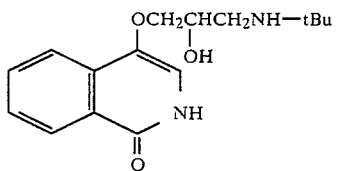

II (Compound of the invention)

EXP. I. β-BLOCKING ACTIVITY IN VITRO

A β-adrenergic blocking activity of compounds I and II in isolatd guinea pig atria was measured in terms of a blockade of isoproterenol-induced increase in beat rate. The result is set forth in the table below.

EXP. II β-BLOCKING ACTIVITY IN VIVO

The β-adrenergic blocking activity after i.v. administration was obtained by using the method of Y. Yabuuchi et al. [Jap. J. Pharmacol. 24, 853 (1974)]. The result is set forth in the table below.

EXP. III DURATION OF β-BLOCKING ACTIVITY

The 50%-blockade duration of the β-blocking activity after oral administration of compounds I and II at 0.2 mg/kg in conscious dogs was measured in terms of hours by the method of Lee et al [Europ. J. Pharmacol. 33, 371 (1975)]. The result obtained is set forth in the table below.

TABLE

| | Relative potency of compounds I and II (compound I:100) | |
|---|---|---|
| | Compound I | Compound II |
| Exp. I | 100 | 1000 |
| Exp. II | 100 | 250 |
| Exp. III | 10 hrs. | 24 hrs. |

Isocarbostyril derivatives of the present invention, as apparent from the above, are more potent than the known 2-methyl derivatives in man and animal bodies.

Now referring to the following examples, the present invention will be explained more precisely.

EXAMPLE 1

A mixture of 1.30 g of 4-(2,3-epoxy)propoxyisocarbostyril, 2.19 g of tertiary-butylamine and 15 ml of methanol was refluxed with stirring for 3 hours, then concentrated under reduced pressure. After adding methanol to the concentrate, the solution was further concentrated under reduced pressure. The residual thus formed was dissolved in 25 ml of acetone, to which 6N hydrogen chloride-isopropylalcohol solution was added to make acidic slightly. A crystal thus formed was taken out by filtration, washed with acetone and then dried in vacuo. The crystal was recrystallized from methanol-acetone mixed solution to yield 1.38 g of 4-(3-tertiary-butylamino-2-hydroxy)propoxyisocarbostyril hydrochloride, as white crystalline powder. m.p. 218°–223° C.

IR(cm$^{-1}$)(Nujol): 3300, 3200, 1650, 1640, 1610.

NMR(DMSO-d$_6$): δ1.36(9H, s), δ3.18(2H, broad), δ4.10(2H, broad), δ4.33(1H, broad), δ4.84(1H, broad, disappeared by D$_2$O addition), δ6.83(1H, s), δ7.37-8.40(4H, m), δ9.05(2H, broad, disappeared by D$_2$O addition), δ11.20(1H, s, disappeared by D$_2$O addition).

EXAMPLE 2

A mixture of 1.30 g of 4-(2,3-epoxy)propoxyisocarbostyril, 2.18 g of secondary-butylamine and 20 ml of methanol was refluxed for 3 hours with stirring. Then by treating in the same manner as in the Example 1, 1.22 g of 4-(3-secondary-butylamino-2-hydroxy)propoxyisocarbostyril hydrochloride was obtained as white crystalline powder. m.p. 173°–175° C.

IR(cm$^{-1}$)(Nujol): 3340, 3170, 1690, 1650, 1608.

NMR(DMSO-d$_6$): δ0.92(3H, t, J=7 Hz), δ1.30(3H, d, J=7 Hz), δ1.36-2.20(2H, m), δ3.20(3H, broad), δ4.00(2H, broad), δ4.36(2H, broad), δ5.35(1H, broad, disappeared by D$_2$O addition), δ6.87(1H, s), δ7.37-8.40(4H, m), δ9.00(2H, broad, disappeared by D$_2$O addition), δ11.10(1H, s, disappeared by D$_2$O addition).

EXAMPLE 3

A mixture of 1.30 g of 4-(2,3-epoxy)propoxy isocarbostyril, 2.56 ml of isopropylamine and 20 ml of methanol was refluxed for 3 hours with stirring. Then by treating in the same manner as in the Example 1. 1.18 g of 4-(2-hydroxy-3-isopropylamino)propoxyisocarbostyril hydrochloride was obtained as white crystalline powder. m.p. 188°–193° C.

IR(cm$^{-1}$)(Nujol): 3350, 3170, 1690, 1650, 1608.

NMR(DMSO-d$_6$): $\delta$1.32(6H, d, J=6 Hz), $\delta$3.20(2H, broad), $\delta$3.40(1H, broad), $\delta$4.05(2H, broad), $\delta$4.43(1H, broad), $\delta$6.03(1H, broad, disappeared by addition of D$_2$O), $\delta$6.83(1H, s), $\delta$7.38–8.35(4H, m), $\delta$9.05(2H, broad, disappeared by addition of D$_2$O), $\delta$11.18(1H, broad, disappeared by addition of D$_2$O).

REFERENCE EXAMPLE 16.1 g of 4-hydroxyisocarbostyril was suspended in 160 ml of methanol, 21.1 g of 28% sodium methylate was added thereto to dissolve, and then 68.5 g of epibromohydrin was added and stirred for 1 hour at inner temperature of 60° C. The resulting reaction mixture was then concentrated under reduced pressure, and the residue obtained was extracted by adding water and chloroform. The chloroform layer thus obtained was washed with a saturated saline solution, dried over anhydrous sodium sulfate, then concentrated under reduced pressure. 11.8 g of the residue was dissolved in a mixed solvent of chloroform and methanol (19:1), purified over a column packed with 100 g of silica gel to obtain 5.0 g of the main fraction. The fraction was then dissolved in a mixed solvent of methanol and chloroform (1:1), then cooled after addition of acetone to separate a crystal. The crystal was taken out by filtration and then dried in vacuo to obtain 4.0 g of 4-(2,3-epoxy)propoxyisocarbostyril. m.p. 145°–149° C.

IR(cm$^{-1}$)(Nujol): 1690, 1650, 1610

NMR(CDCl$_3$): $\delta$2.67–3.05(2H, m), $\delta$3.25–3.57 (1H, m), $\delta$3.67–4.40(2H, m), $\delta$6.78(1H, s), $\delta$7.35–8.55(4H, m), $\delta$12.30(1H, s, disappeared by addition of D$_2$O).

Fractions obtained from the subsequent eluation of the column were dissolved in a mixed solvent of methanol and chloroform (1:1), to which solution was then added acetone to separate a crystal. The crystal was taken out by filtration, and then dried in vacuo to obtain 0.7 g of 4-(3-bromo-2-hydroxy)propoxyisocarbostyril. m.p. 197°–200° C.

IR(cm$^{-1}$)(Nujol): 3310, 2950, 1655, 1605.

NMR(DMSO-d$_6$): $\delta$3.67(2H, d, J=4 Hz), $\delta$4.00(2H, d, J=4 Hz), $\delta$4.13(1H, broad), $\delta$6.80(1H, s), $\delta$7.33–8.35(4H, m), $\delta$10.89(1H, s).

Further, an additional feature of the present invention is to use isocarbostyril derivatives of the invention in the form of therapeutic agents or formulations which contain one of the said isocarbostyril derivatives as the active ingredient together with conventional carriers and diluents.

The therapeutic agents or formulations are prepared in a conventional manner by compounding an appropriate dose with the conventional liquid or solid carriers or diluents and the conventional pharmaceutical auxiliaries, in accordance with the desired route of administration.

The preferred formulations are those suitable for oral administration. Examples of these are tablets, film tablets, dragees, capsules, pills, powders, solutions, suspensions or forms which have a depot effect.

Parenteral formulations, such as injection solutions, may of course also be used. Further examples of suitable formulations include suppositories.

Appropriate tablets may be obtained, for example, by mixing the active compound with conventional auxiliaries, for example inert diluents, such as lactose, starch, dibasic calcium phosphate, crystalline cellulose, disintegrating agents, such as corn starch, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate. The tablets may also consist of a plurality of layers.

Accordingly, dragees may be prepared by coating cores, prepared in a similar manner to the tablets, with agents conventionally used in dragee coatings, for example polyvinylpyrrolidone or shellac, gum arabic, talc, titanium dioxide or sugar. The dragee shell can also consist of several layers, in which the auxiliaries, mentioned above in connection with tablets, may be used.

Solutions or suspensions containing the novel active compound may additionally contain sweeteners, eg. saccharin, cyclamate or sugar, and, for example, flavorings, such as vanillin or orange extract. Capsules containing the active compounds may be prepared, for example, by mixing the latter with an inert carrier, such as lactose or sorbitol, and encapsulating the mixture in gelatin capsules.

Suitable suppositories may be prepared, for example, by mixing the active compound with an appropriate carrier for this purpose, such as a neutral fat or polyethylene glycol or derivative thereof.

Individual doses of the novel compounds suitable for man are from 1–300 mg, preferably from 10–150 mg.

The following are illustrative of the typical formulations in which the isocarbostyril derivative of the invention is incorporated as an active ingredients:

| Tablets | |
|---|---|
| (a) Active ingredient | 50.0 mg |
| Lactose | 54.25 mg |
| Crystalline cellulose (Avicel) | 30.0 mg |
| CMC | 15.0 mg |
| Magnesium stearate | 0.75 mg |
| | 150.0 mg |
| (b) Active ingredient | 50.0 mg |
| Calcium phosphate | 54.25 mg |
| Crystalline cellulose (Avicel) | 30.0 mg |
| CMC | 15.0 mg |
| Talc | 0.75 mg |
| | 150.0 mg |
| Capsule | |
| Active ingredient | 25.0 mg |
| Granulated corn starch | 93.5 mg |
| Magnesium stearate | 1.5 mg |
| | 120.0 mg |

What we claim is:
1. 4-(3-tert.-butylamino-2-hydroxy)propoxyisocarbostyril hydrochloride.

* * * * *